US006953482B2

(12) United States Patent
Doi et al.

(10) Patent No.: US 6,953,482 B2
(45) Date of Patent: Oct. 11, 2005

(54) INSTRUMENT FOR REGENERATING LIVING ORGANISM TISSUE OR ORGAN

(75) Inventors: Nobutoshi Doi, Osaka (JP); Kazuhisa Matsuda, Osaka (JP); Ken-ichiro Hata, Kariya (JP); Kensuke Sakai, Aichi (JP)

(73) Assignees: Nipro Corporation, Osaka (JP); Minoru Ueda, Nisshin (JP)

( * ) Notice: Subject to any disclaimer, the term of this patent is extended or adjusted under 35 U.S.C. 154(b) by 0 days.

(21) Appl. No.: 10/132,577

(22) Filed: Apr. 26, 2002

(65) Prior Publication Data

US 2002/0161450 A1 Oct. 31, 2002

(30) Foreign Application Priority Data

Apr. 26, 2001 (JP) ........................................ 2001-129130

(51) Int. Cl.[7] .................................................. A61F 2/36
(52) U.S. Cl. .................................... 623/23.71; 424/426
(58) Field of Search ................................ 606/151, 152, 606/153, 154, 155, 156, 157, 158; 623/23.7, 23.71; 424/426

(56) References Cited

U.S. PATENT DOCUMENTS

| 5,735,863 | A | | 4/1998 | Della Valle et al. ......... 606/152 |
| 5,756,457 | A | * | 5/1998 | Wang et al. .................... 514/12 |
| 5,830,493 | A | * | 11/1998 | Yokota et al. ............... 424/426 |
| 5,834,029 | A | * | 11/1998 | Bellamkonda et al. ...... 424/570 |
| RE36,370 | E | * | 11/1999 | Li ............................... 424/443 |
| 6,090,117 | A | * | 7/2000 | Shimizu ...................... 606/152 |
| 6,156,572 | A | * | 12/2000 | Bellamkonda et al. ...... 435/395 |
| 6,214,021 | B1 | * | 4/2001 | Hadlock et al. ............ 606/152 |

FOREIGN PATENT DOCUMENTS

| EP | 0 945 145 A1 | 9/1999 |
| JP | 5-237139 A | 9/1993 |
| WO | 02/47557 A1 | 6/2002 |

OTHER PUBLICATIONS

Archibald, S. J. et al.; "A Collagen–Based Nerve Guide Conduit for Peripheral Nerve Repair: An Electrophysiological Study of Nerve Regeneration in Rodents and Nonhuman Primates"; *The Journal of Comparative Neurology*; vol. 306, pp. 685–696; 1991.

Itoh, S. et al.; "Synthetic Collagen Fibers Coated with a Synthetic Peptide Containing the YIGSR Sequence of Laminin to Promote Peripheral Nerve Regeneration in vivo"; *Journal of Materials Science: Materials in Medicine*; vol. 10, pp. 129–134; 1999.

Tong, X. et al.; "Sciatic Nerve Regeneration Navigated by Laminin–Fibronectin Double Coated Biodegradable Collagen Grafts in Rats"; *Brain Research*, vol. 663, pp. 155–162; 1994.

Colin, W. et al.; "Nerve Regeneration Through Collagen Tubes"; *J. Dent. Res.*, vol. 63(7), pp. 987–993; 1984.

Itoh, S. et al.; "A Study on Induction of Nerve Regeneration Using Bioabsorbable Tubes"; *J. Jpn. Soc. Surg. Hand.*; vol. 17(4), pp. 371–375; 2000.

Suzuki, K. et al.; "Development of PGA–Collagen Channel for Peripheral Nerve Regeneration–Functional Evaluation"; *Jpn. J. Artif. Organs*; vol. 27(2), pp. 490–494; 1998.

(Continued)

Primary Examiner—Corrine McDermott
Assistant Examiner—Thomas J Sweet
(74) Attorney, Agent, or Firm—Kubovcik & Kubovcik

(57) ABSTRACT

This invention relates to an instrument for regenerating a living organism tissue or organ, characterized in that a support (A) formed from a biodegradable material or a bioabsorbable material includes a sponge-like fine matrix (B) formed from a biodegradable material or a bioabsorbable material and a linear guide channel (C) for a living organism tissue or organ.

17 Claims, 8 Drawing Sheets

OTHER PUBLICATIONS

Kiyotani, T. et al.; "Peripheral Nerve Regeneration in a PGA–Collagen Composite Tube"; *Jpn J. Artif. Organs*; vol. 25(2), pp. 476–480; 1996.

Shimada, H. et al.; "Induction of Peripheral Nerve Regeneration Using Laminin–Fibronectin Double Coated Collagen Fiber Grafts"; *Jpn. J. Artif. Organs*; vol. 22(2), pp. 359–363; 1993.

Kline, D. G. et al., "The Use of a Resorbable Wrapper for Peripheral–Nerve Repair"; *Journal of Neurosurgery*; vol. 21(9), pp. 737–750; 1964.

Reid, R. L. et al., "Biodegradable Cuff an Adjunct to Peripheral Nerve Repair: A Study in Dogs"; *The Hand*; vol. 10, No. 3, pp. 259–266; 1978.

Henderson, C. E. et al.; "Denervation Increases a Neurite–promoting Activity in Extracts of Skeletal Muscle"; *Nature*; vol. 302, pp. 609–677; 1983.

Mackinnon, S. E.; "Nerve Regeneration Through a Pseudosynovial Sheath in a Primate Model", *Plastic and Reconstructive Surgery*; vol. 75, No. 6, pp. 833–839; 1985.

Nishimune, H. et al.; "Neurocrescin: A Novel Neurite–outgrowth Factor Secreted by Muscle After Denervation"; *NeuroReport*; vol. 8, pp. 3649–3654; 1997.

Ochi, M. et al.; "Promotion of Sciatic Nerve Regeneration in Rats by a New Neurotrophic Pyrimidine Derivative MS–430"; *Gen. Pharmac.*; vol. 26, No. 1, pp. 59–64; 1995.

Mackinnon, S. E. et al.; "Clinical Nerve Reconstruction with a Bioabsorbable Polyglycolic Acid Tube"; *Plastic and Reconstructive Surgery*; vol. 85, No. 3, pp. 419–424; 1990.

Aebischer, P. et al.; "Regeneration of Transected Sciatic Nerves Through Semi–Permeable Nerve Guidance Channels"; *Trans Am Soc Artif Intern Organs*; vol. XXXII, pp. 474–477; 1986.

McDonald, J. W.; "Transplanted Embryonic Stem Cells Survive, Differentiate and Promote Recovery in Injured Rat Spinal Cord"; *Nature Medicine*; vol. 5, No. 12, pp. 1410–1412; 1999.

Uyeda, A. et al.; "MDP77: A Novel Neurite–Outgrowth–Promoting Protein Predominantly Expressed in Chick Muscles"; *Biochemical and Biphysical Research Communications*; vol. 269, pp. 564–569; 2000.

Pu, L. et al.; "Effects of Nerve Growth Factor on Nerve Regeneration Through a Vein Graft Across a Gap"; *Plastic and Reconstructive Surgery*; vol. 104, No. 5, pp. 1379–1385; 1999.

Sunderland, S.; "A Classification of Peripheral Nerve Injuries Producing Loss of Function"; *Brain*; vol. 74, , No. 4, pp. 491–516; 1951.

Wakabayashi, Y. et al.; "Regeneration of Motor Nerve"; *Inflammation and Immunity*; vol. 9, No. 3, pp. 271–277; 2001.

Itoh, S. et al.; "Regernation of Motion Nerve and Artficial Nerve"; *Modern Treatment*; vol. 31, No. 12, pp. 115–123; 1999.

Wakabayashi, Y. et al.; "Artificial Nerve for Regeneration of Motion Nerve"; *Clinical Neuroscience*; vol. 18, No. 11, pp. 1280–1283; 2000.

\* cited by examiner

INSTRUMENT FOR REGENERATING LIVING ORGANISM TISSUE OR ORGAN

TECHNICAL FIELD OF THE INVENTION

The present invention relates to an instrument for regenerating a living organism tissue/organ. More particularly the present invention relates to an instrument for regenerating a human tissue or organ, for example, a nerve fiber, a micro blood vessel, or the like, which was cut due to lesion or injury.

BACKGROUND OF THE INVENTION

In a case where a human tissue or organ such as a nerve or tendon is injured due to an accident, disaster or disease and the injury cannot be cured by self-recovery of a patient, a disorder occurs in perception, sensation, mobility or the like. For such a patient, with the development of a technology for connecting injured areas under a microscope in recent years, therapeutics such as surgical suturing for connecting cut portions or nerve autotransplantation, by which a nerve or tendon of a patient himself or herself biopsied from another part of the body is transplanted to recover the lost function, has been effective.

However, when the injured region is too large, restoration by the above-mentioned connection is impossible and it has been necessary to obtain a nerve from another location where a disorder, if any, could be believed to be less important than the disorder of the injured portion of concern and transplant it to the injured portion. In this case, although it is less important than the disorder at the portion where injury first occurred, the nerve at another location that has received no injury and is healthy is biopsied, resulting in a disorder in perception, sensation or mobility being generated at that location.

As one example of nerve autotransplantation, there may be mentioned one including, first, a biopsy of a sura nerve and then transplanting of the nerve to an injured location. In this case, the problem is that usually skin sensation, etc. of the area from ankle to instep is lost. Accordingly, there has been a keen demand for a therapeutic method that enables restoration of the injured area without causing any impediment to another area (ankle, etc.).

To overcome the drawbacks of nerve autotransplantation, various studies have been made with a view to recovery of original functions by substituting an injured area with an artificial instrument. For example, attempts have been made in which a ruptured portion of a nerve is covered by a tubular structure (also called a covering material) made of a non-absorbable material which is not absorbed by the human body (silicon compounds, fluorine compounds and various synthetic polymers) with the expectation of growth and proliferation of new nerve cells from the cut nerve in the tubular member so that the cut nerve portion can be grafted again. (Ducker et al., Journal of Neurosurgery, 28, 582–587 (1968); Midgler et al., Surgical Forum, 19, 519–528 (1968); Lundborg et al., Journal of Neuropathology in Experimental Neurology, 41, 412–422 (1982); Molander et al., Muscle & Nerve, 5, 54–58 (1982); Uzman et al., Journal of Neuroscience Research, 9, 325–338 (1983); Nyilas et al., Transactions American Society of Artificial Internal Organs, 29, 307–313 (1983); U.S. Pat. No. 4,534,349, etc.)

In these experiments, although some cell proliferation is observed at the both ends of the cut nerve, no recovery by grafting the cut nerve is attained. The reason for this is that when cells proliferate, generally they adhere to the tubular structure. From this position they proliferate in such a direction that they cover the cut portion but mere covering of the cut portion leaves a gap between the cut ends and proliferation of cells is terminated before the cells completely fill the cut portion, so that restoration of the cut gap is not achieved.

Also, since the implanted tubular structure (also called a covering material) is artificially synthesized, it exists as a foreign matter in the body forever, which is undesirable. Accordingly, to overcome the problem of the residual foreign matter, there is an example in which such a tubular structure is substituted by a bioabsorbable material (Suzuki et al., Artificial Organs, 27(2), 490–494 (1998)). Although use of a bioabsorbable material for the tubular structure solves the problem of residual foreign matter in the body, the problem of the existence of a gap still remains to be solved and it has been difficult to restore the deficit portion by cell proliferation.

Furthermore, to solve the problem of a gap inside the tubular structure made of a bioabsorbable material, an attempt has been made in which a fiber bundle of collagen is inserted and coated with fibronectin (FN) (Japanese Patent Application Laid-open No. Hei 5–237139, Hiroki Shimada, et al., Artificial Organ, 22(2), 359–363, 1993). In this case, although the problem of the residual foreign matter in the body and the problem of the existence of a gap may be solved, the following problems still remain. That is, the collagen fiber bundle is thin and tends to be cut so that it is difficult to handle it and also it is difficult to insert it in a tubular structure such that it fully fills the inside of the tubular structure. If the filling amount of the fiber bundle is decreased in order to facilitate insertion, there occur various defects that the gap between the fibers increases, the fiber bundle cannot be fixed well, localization of the fiber bundle inside the tubular member occurs and so on. Therefore, both cases are undesirable since the gap inside is increased, giving the same results as those of the case where the above-mentioned gap is large.

Also, in the case where the filling amount of the fiber bundle is increased, other problems remain. That is, when the collagen fiber is filled so that there can occur no localization of the fiber in the inside of the tubular structure, the filling ratio of the lumen of the tubular structure increases but the space for cell proliferation become narrow. Furthermore, in order for cells to efficiently proliferate, nutrients that the cells need must be quickly supplied and waste products generated by metabolism must be quickly removed. However, when the fiber bundle is inserted in a high filling density, exchange of substances is more inhibited closer to the central portion of the fiber bundle, so that it cannot be said that the environment is suitable for cell proliferation and, therefore, the fiber bundle is not suitable for restoring the nerve by cell proliferation.

Also, as a means for providing more efficient cell proliferation, a tubular structure encapsulating therein a cell growth factor has been reported (U.S. Pat. No. 4,963,146). In addition, a tubular structure coated on the surface of the lumen with fibrinogen, fibronectin or the like (Non-toxic Nerve Guide Tubes Support Neovascular Growth in Transected Rat Optic Nerve, R. Madison et al., Experimental Neurology, 86(3): 448–461, 1984), a tubular structure filled in the lumen thereof with fiber coated with laminin (Japanese Patent Application Laid-open No. Hei 5-237139, Hiroki Shimada, et al., Artificial Organ, 2:2(2), 359–363, 1993) and the like are known. However, when a growth factor or the like is coated on the surface of the lumen, the surface area is limited and the cell growth factor does not reach cells remote from the coated wall surface since the cells proliferate three-dimensionally. Also, when the cell growth factor is coated on the fiber filling the lumen, although the coating surface area is larger than the surface area of the lumen, the amount of the cell factor with respect to the volume of the lumen decreases because of the volume of the filled fiber.

SUMMARY OF THE INVENTION

An object of the present invention is to provide, in place of the conventional tubes for transplanting a nerve or a blood vessel, an instrument for regenerating a living organism tissue or organ which is free of the problem of a residual foreign matter in the body and the problem of a gap and into which the nerve, the blood vessel or the like can be readily inserted to enable cells to efficiently grow three-dimensionally.

In consideration of the above-mentioned circumstances, the present inventors have made extensive studies and as a result they have found that a sponge-like fine matrix in the lumen of a tubular structure made of a bioabsorbable material or biodegradable material and formed so as to have a suitable density to provide a footing for cells to regenerate in a void portion inside the tubular structure can hold various growth factors secreted by surrounding cells or artificially injected due to the characteristics of a porous material possessed by the sponge-like fine matrix and thereby increase proliferation efficiency of various cells, for example, nerve cells. Also, by forming a linear structure for giving directivity to the growth of cells being regenerated and for guiding the growth of the cells, the time in which cells being regenerated between the deficit tissues or organs are grafted to the target tissue is reduced. As a result an instrument for regenerating a living organism tissue or organ which allows the living organism tissue or organ to quickly regenerate, has high bioabsorbability, and leaves no residual foreign matter in the body has been completed.

That is, the present invention relates to:
(1) an instrument for regenerating a living organism tissue or organ, comprising a support (A) formed from a biodegradable material or a bioabsorbable material, a sponge-like fine matrix (B) formed from a biodegradable material or a bioabsorbable material and a linear channel (C) for guiding a living organism tissue or organ,
(2) an instrument for regenerating a living organism tissue or organ according to the above item 1, wherein the biodegradable material is decomposed by a decomposing enzyme in the living organism, acid or alkali, and is a protein, a polypeptide or a derivative thereof,
(3) an instrument for regenerating a living organism tissue or organ according to the above item 1, wherein each of the bioabsorbable materials is a porous substance which allows permeation of body fluid and is a protein, a polypeptide, or a derivative thereof, a polysaccharide or a derivative thereof, polylactic acid, polyglycolic acid, a copolymer of glycolic acid and lactic acid, a copolymer of lactic acid and ε-amino-caproic acid or an aliphatic polyester,
(4) an instrument for regenerating a living organism tissue or organ according to the above item 1, wherein the support (A) formed from the biodegradable material or the bioabsorbable material is tubular,
(5) an instrument for regenerating a living organism tissue or organ according to any one of the above items 1 to 4, wherein the support (A) formed from the biodegradable material or the bioabsorbable material is tubular and is constituted by a fibrous material,
(6) an instrument for regenerating a living organism tissue or organ according to the above item 5, wherein the fibrous material comprises short fibers, long fibers, filaments, a floc, a textile fabric, or a non-woven fabric,
(7) an instrument for regenerating a living organism tissue or organ according to the above item 1, wherein the sponge-like fine matrix (B) is a collagen sponge layer,
(8) an instrument for regenerating a living organism tissue or organ according to the above item 1, wherein the linear channel (C) for guiding the living organism tissue or organ comprises at least one fiber inserted into the inside of the support (A) in the longitudinal direction thereof,
(9) an instrument for regenerating a living organism tissue or organ according to any one of the above items 1 to 8, wherein the linear channel (C) for guiding the living organism tissue or organ is at least one tubular structure and is formed in the inside of the support (A) in the longitudinal direction thereof,
(10) an instrument for regenerating a living organism tissue or organ according to any one of the above items 1 to 9, wherein the linear channel (C) for guiding the living organism tissue or organ is embedded in the sponge-like fine matrix (B),
(11) an instrument for regenerating a living organism tissue or organ according to any one of the above items 1 to 10, wherein the support (A) is a tubular structure comprising a bundle of collagen fibers, the sponge-like fine matrix (B) is a collagen sponge layer provided in the inside of the tubular structure, and the linear channel (C) for guiding the living organism tissue or organ is a fiber or a tubular structure penetrating the collagen sponge layer therethrough,
(12) an instrument for regenerating a living organism tissue or organ according to any one of the above items 1 to 11, wherein the living organism tissue or organ is a blood vessel, a trachea, an esophagus, intestine, a tendon (ligament) or a nerve of a human primate, a nonhuman primate or a rodent,
(13) an instrument for regenerating a living organism tissue or organ, which comprises at least one linear structure (c) provided so as to penetrate a sponge layer (b) therethrough in the longitudinal direction in the inside of the tubular structure (a), wherein a tubular structure (a) is formed by a bundle of collagen fibers having a fiber diameter of about 5 to 1,000 μm, and has an outer diameter of about 0.1 to 50 mm, and an inner diameter of about 0.05 to 40 mm, and is provided with a fine collagen sponge layer (b) having a porosity of about 70 to 99.9% inside the tubular structure,
(14) an instrument for regenerating a living organism tissue or organ according to the above item 13, wherein at least one linear structure (c) is formed from a collagen fiber having a fiber diameter of about 5 to 1,000 μm,
(15) an instrument for regenerating a living organism tissue or organ according to the above item 13 or 14, wherein the linear structure is provided with at least one tubular communicating passage having a pore diameter of about 5 to 1,000 μm,
(16) an instrument for regenerating a living organism tissue or organ according to the above item 13, wherein at least one linear structure (c) is a channel for guiding regeneration of a peripheral or spinal nerve, and
(17) an instrument for regenerating a living organism tissue or organ according to the above item 1, wherein the linear channel (C) for guiding a living organism tissue or organ is a channel for guiding regeneration of a peripheral or spinal nerve.

DESCRIPTION OF THE DRAWINGS

In FIG. 1, reference numeral 1 designates a collagen support, reference numeral 2 designates a collagen fiber, and reference numeral 3 designates a collagen sponge layer.

DETAILED DESCRIPTION OF THE INVENTION

Figure 1:
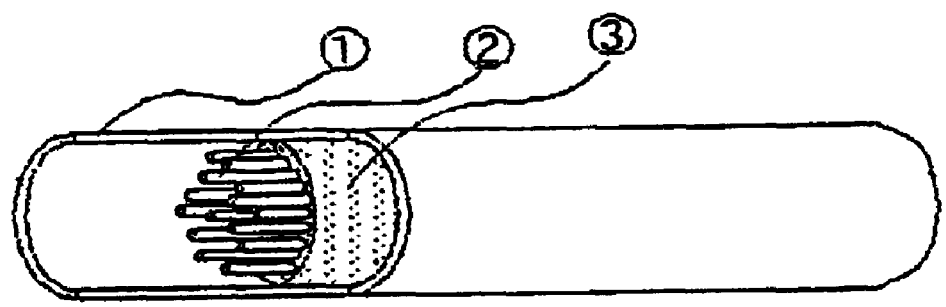
FIG. 1 is a schematic diagram showing an instrument for regenerating a living organism tissue or organ of the present invention.

In the present invention, examples of the living organism tissue or organ include a blood vessel, trachea, esophagus, intestine, tendon (ligament) and nerve of a human primate, a nonhuman primate or a rodent. The tissue used in the present invention is preferably a human nerve, such as a peripheral nerve or a spinal nerve.

In the present invention, the support (A) formed from a biodegradable material or a bioabsorbable material means a molded article having a shape of a tubular structure (including a hollow structure), a flat plate, a curved plate and the like, which is selected depending on the living organism tissue or organ to be regenerated. In particular, the tubular structure performs the function of maintaining a space for regenerating a living organism tissue or organ against the permeation of the surrounding tissue.

The support (A) used in the present invention preferably includes a tubular structure, a stent and the like which have a shape of a tubular structure (including a hollow structure), a plate-like structure, or a gel or the like and is constituted by a fibrous material made of a biodegradable material or a bioabsorbable material. The fibrous material includes, for example, short fibers, long fibers, filaments, a floc, a textile fabric, a non-woven fabric and so forth. The fiber diameter of the fibrous material is about 5 to 1,000 μm, preferably 10 to 100 μm. In particular, an inter-fiber interval of the support (A) is 0 to 200 μm, preferably 0 to 100 μm.

The biodegradable material used in the present invention is a material that is decomposed by a decomposing enzyme in a living organism, acid or alkali, characterized by being porous to allow permeation of body fluid. Examples include proteins such as collagen and gelatin, polypeptides, and derivatives thereof.

Further, the bioabsorbable material is a porous substance which allows permeation of body fluid, for example, a protein or a polypeptide, or a derivative thereof, a polysaccharide or a derivative thereof, polylactic acid, polyglycolic acid, a copolymer of glycolic acid and lactic acid, a copolymer of lactic acid and ε-aminocaproic acid, or an aliphatic polyester such as a lactide polymer (Japanese Patent No. 2939750).

The origin of collagen used in the present invention is not limited and generally its origin includes cows, pigs, birds, fish, primate, rabbits, sheep, rats, humans and so forth. The collagen can be obtained from skin, tendon, bone, cartilage, internal organs or the like by various known extracting methods. However, the origin is not limited to these specific sites. Furthermore, the type of collagen used in the present invention is not limited to a particular classifiable type but in consideration of handling, types I, III and IV are preferable.

Production of the support (A) from these materials is performed according to a conventional method.

In the present invention, one auxiliary means for regenerating a living organism tissue or organ is a sponge-like fine matrix (B), which is constituted, for example, by a collagen sponge layer, collagen fiber or the like. The sponge-like fine matrix (B) gives suitable density and footing to cells in the living organism tissue or organ which is to be regenerated in the inside thereof. Also, short fibers, a floc, a non-woven fabric and the like constituted by the collagen fiber are expected to have similar effects.

Furthermore, another auxiliary means is a linear guide channel (C), which gives directivity of growth to cells being regenerated, to thereby reduce the time needed for grafting of the cells to the target tissue or organ. The guide channel (C) is specifically a tubular structure constituted by a number of long fibers, filaments, fabric, knitted fabric or a hollow tubular structure.

The hollow tubular structure form of guide channel (C) can be formed by inserting a substrate during molding of the sponge-like matrix (B) and then removing the substrate after the molding.

A specific example of the instrument for regenerating a living organism tissue/organ of the present invention includes one in which the support (A) is a hollow tubular structure which comprises a biodegradable material or bioabsorbable material and inside the lumen a fine matrix (B) and a linear guide channel (C) are provided as the above-mentioned auxiliary means. The tubular structure (A) is a molded product of a bundle of collagen fibers, provided with a collagen sponge layer (B) inside the tubular structure and a collagen fiber inserted so as to penetrate the sponge layer or a tubular communicating passage (C).

For example, the instrument for regenerating a living organism tissue or organ of the present invention has a channel for guiding regeneration of a peripheral nerve or spinal nerve, and comprises a tubular structure (a) constituted by a bundle of collagen fibers with a fiber diameter of about 5 to 1,000 μm, preferably 10 to 100 μm, having an outer diameter of about 0.1 to 50 mm, preferably 0.5 to 25 mmm, and an inner diameter of about 0.05 to 40 mm, preferably 0.3 to 20 mm, and provided with a collagen sponge layer (b) on an inner surface thereof, and a collagen fiber inserted so as to penetrate the sponge layer therethrough in the longitudinal direction along the hollow structure or a tubular communicating passage (c).

In the above-mentioned instrument, the collagen sponge layer (b) has a porosity of about 70 to 99.9%, preferably 80 to 99.9%, and may have at least one linear guide channel (c) so as to penetrate therethrough in the longitudinal direction. The linear guide channel (c) comprises collagen fiber or a tubular communicating passage. In the case of collagen fiber, it has a diameter of about 5 to 1,000 μm, preferably 10 to 100 μm and an insertion amount corresponding to 5 to 70%, preferably 10 to 60% with respect to the inner volume of the tubular structure (a). In the case of the tubular communicating passage (c), it has a diameter of about 5 to 1000 μm, preferably 10 to 100 μm and a volume occupying in a ratio of 5 to 70%, preferably 10 to 60%, with respect to the inner volume of the tubular structure (a).

One embodiment of the present invention is an instrument for regenerating a living organism tissue or organ, which has a tubular structure (a) constituted by a bundle of collagen fibers with a fiber diameter of about 10 to 100 μm, and having an outer diameter of about 0.5 to 20 mm and an inner diameter of about 0.3 to 15 mm, and which has a collagen sponge fine layer (b) with a porosity of about 70 to 99.9% inside the tubular structure, and which has at least one linear structure (c) provided so as to penetrate the sponge layer (b) therethrough inside the tubular structure (a) in the longitudinal direction.

Another embodiment of the present invention is an instrument for regenerating a living organism tissue or organ having a channel for guiding the regeneration of a peripheral nerve or spinal nerve, which has a tubular structure (a') constituted by a bundle of collagen fibers with a fiber diameter of about 10 to 100 μm, and having an outer diameter of about 0.5 to 20 mm and an inner diameter of about 0.3 to 10 mm, a collagen sponge layer (b') with a porosity of about 70 to 99.9% inside the tubular structure, and as a linear guide channel (c'), collagen fiber with a diameter of 5 to 1,000 μm in an amount corresponding to 5 to 70% of the volume of lumen portion or a tubular structure with a diameter of 5 to 1,000 μm in a volume of 5 to 70% of the lumen portion, inserted or formed, respectively, so as to penetrate the sponge layer therethrough.

Furthermore, an embodiment of the present invention is an instrument for regenerating a living organism tissue or organ having a channel for guiding regeneration of a peripheral nerve or a spinal nerve, and which has a tubular structure (a") constituted by a bundle of collagen fibers with a fiber diameter of about 10 to 100 μm, and having an outer diameter of about 0.5 to 20 mm and an inner diameter of about 0.3 to 10 mm, and which has a collagen sponge layer (b") with a porosity of about 70 to 99.9% inside the tubular structure, and, as a linear guide channel (c"), collagen fiber with a diameter of 10 to 100 μm in an amount corresponding to 10 to 60% of the volume of the lumen portion or a tubular structure with a diameter of 10 to 1,000 μm in a volume of 10 to 60% of the lumen portion, inserted or formed, respectively, so as to penetrate the sponge layer therethrough.

The instrument of the present invention preferably has an opening space for inserting a nerve on both ends of the tubular structure.

A method for producing the instrument of the present invention is described in detail below.

First, a fibrous material, for example, short fibers, long fibers, filaments, a floc, a textile fabric, a non-woven fabric or the like is produced from a solution of a biodegradable material or a bioabsorbable material, for example, collagen, according to a conventional method and then a tubular structure is produced from the fibrous material.

The solvent for dissolving the collagen may be any known substance but use of water according to a conventional method is preferred. The concentration of the collagen solution is 0.1 to 30 wt %, preferably 0.5 to 10 wt %.

The extrusion molding method for producing a collagen fiber is not particularly limited but usually the coagulating liquid is ethyl alcohol and the extrusion rate is about 100 to 500 mm/sec. Cooling of the fiber taken out from the coagulating liquid may be performed in the neighborhood of the degeneration temperature of collagen or less, i.e. at about 40° C. or less, but preferably is maintained at 4 to 20° C. The diameter of the fiber is preferably about 10 to 100 μm.

To produce the support (A), for example, a tubular structure (including a hollow structure) from the above-mentioned fibrous material, a continuous fiber produced from a collagen solution can be wound around a rod-like substrate having a predetermined length to obtain a continuous fiber bundle having a uniform fiber direction. By removing the rod-like substrate, the fiber bundle forms a hollow tubular structure. In the case where the tubular structure is used for restoring or regenerating a nerve such as a peripheral nerve or a spinal nerve, the tubular structure preferably has a suitable wall thickness of about 0.1 to 5 mm, an outer diameter of about 0.3 to 20 mm, an inner (lumen) diameter of about 0.1 to 10 mm and any desired length. The diameter of the lumen portion depends on the diameter of the nerve to be grafted but in particular a range of from about 0.5 to 10 mm is suitable.

To provide the auxiliary means for regenerating a living organism tissue or organ in the lumen portion of the tubular structure serving as the support (A), the following method may be used. For example, a sponge-like fine matrix (B) filled in the inner (lumen) portion of the tubular structure is produced by injecting a collagen solution in the lumen portion of the support and subjecting it to natural drying, vacuum drying, vacuum lyophilization or a like method. In order to form uniform sponge-like fine matrix (B), it is preferable to form it by a vacuum lyophilization method in which the matrix is frozen after filling the collagen solution in the lumen portion of the support and dried under vacuum. The concentration of the collagen solution is 0.05 to 30%. The drying condition is preferably the maintaining of a vacuum of about 0.08 Torr or less after the collagen solution is frozen.

The sponge-like fine matrix (B) means a state where there is formed a porous material having many domains with vacant spaces of a uniform or non-uniform size dispersed continuously or discontinuously when visually judged or observed under a microscope.

The matrix of a sponge layer formed in the lumen is produced by varying the concentration of the collagen solution used and filling a solution having a higher collagen concentration and a decreasing collagen concentration in sequence. By adjusting the concentration of the collagen solution to be filled, a matrix having layers with different vacant spaces can be obtained and various forms of a matrix depending on the utility can be formed.

When expressing the ratio of the weight of the collagen filled in the lumen to the volume of the lumen of the tubular structure as a filling ratio, the filling ratio is preferably about 0.05 to 30% and, more preferably, the filling ratio is about 0.5 to 15%.

The instrument for regenerating a living organism tissue or organ of the present invention is sutured to an injured tissue or organ in the living organism by a conventional method and is left in the living organism until it recovers naturally. Suturing means in which a predetermined tissue is sutured with an instrument by an ordinary suture are employed.

In the case of a cut nerve, regeneration of the nerve is observed by merely suturing the nerve ends at the ends of the tubular structure (A) at plural points.

Hereinafter, the present invention will be illustrated in detail by way of examples. However, the present invention is not limited thereto.

EXAMPLE 1

Figure 2:
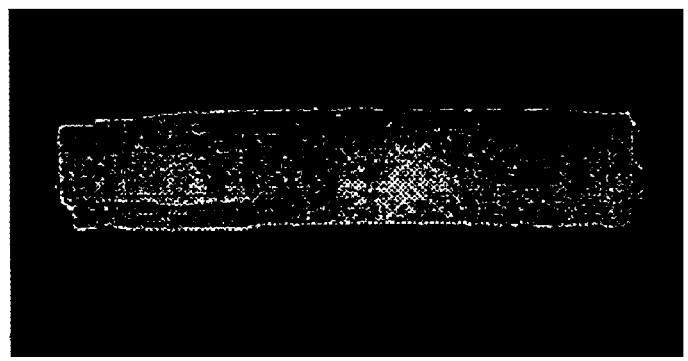
FIG. 2 is a photograph in lieu of a drawing, showing the instrument for regenerating a living organism tissue or organ of Example 1 of the present invention.
Figure 3:
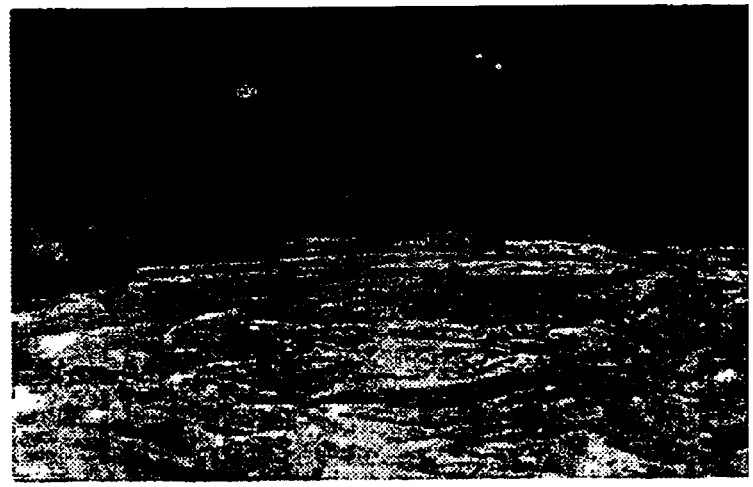
FIG. 3 is a photograph in lieu of a drawing, showing a cross section of the instrument for regenerating a living organism tissue or organ of the present invention.

Production of an Instrument for Regenerating a Living Organism Tissue or Organ Enzyme-solubilized collagen (a mixture of collagen type I and type III) was dissolved in water to prepare an aqueous 5% solution and extruded in a coagulating liquid according to a conventional method to produce a collagen fiber having a diameter of 50 $\mu$m. The collagen fiber obtained was wound around a metal mandrel to produce a tubular structure constituted by the collagen and having an inner diameter of 1 mm and a thickness of 0.5 mm. In its lumen, 200 collagen fibers having a diameter of 50 $\mu$m were simultaneously inserted together with the aqueous 5% collagen solution and rapidly frozen and then lyophilization was performed in vacuo to produce a tubular instrument for regenerating a living organism tissue or organ entirely constituted by the collagen and of a structure such that it has a collagen fiber filling ratio of 50% in the lumen portion and a collagen-made porous material having a porosity of 95% covers each fiber. FIG. 1 is a partial cross sectional view showing the above-mentioned instrument for regeneration. FIG. 2 is a side view of the instrument. FIG. 3 is an enlarged view of the instrument. In FIG. 1, reference numeral 1 designates the collagen support, reference numeral 2 designates the collagen fiber, and reference numeral 3 designates the collagen sponge layer.

Test for Tissue Regeneration

Using the produced instrument for regeneration, a test for tissue regeneration was performed on rats. As the tissue to be regenerated, a rat peripheral nerve was selected.

Figure 4:
FIG. 4 is a photograph in lieu of a drawing, showing a transplanted site of the instrument for regenerating a living organism tissue or organ of the present invention.

The rat fibula nerve was cut to make a 10-mm deficit portion. In this site the tubular collagen-made instrument for regeneration of organ previously cut to 10 mm, i.e., the same length as the deficit length, and subjected to 25-kGy $\gamma$-ray sterilization treatment was inserted and the both ends thereof were sutured and fixed to the cut ends of the nerve with 10-0 polyamide based surgical suture at plural points (FIG. 4). Also, as a control group, a 10-mm deficit portion was made in another rat group similarly in the fibula nerve portion and the wound site was sutured with the surgical suture.

Experimental Results

After the transplantation, a footprint evaluation for evaluating the recovery of the nerve with lapse of time and an observation of nerve fiber regeneration on the twelfth week by cutting out the tissue at the transplanted site and performing an immunological tissue staining of protein gene product 9.5 (PGP 9.5) were carried out.

The evaluation method for the footprint was performed by a WTA method (walking tracks analysis). That is, in a case where the fibula nerve was cut, the rat can not walk on its tiptoes so that when the footprint is recorded, the footprint on the side where the nerve was cut is longer than the footprint on the side where the nerve is normal. On the other hand, assuming that the length of the footprint on the normal side is X and the Length of the footprint on the side of the paralyzed nerve is Y, a WTA value was obtained according to the formula [WTA value=(Y−X)/Y] and the recovery of walking function with a lapse of time was evaluated. The results are shown in FIG. 5.

Figure 5:
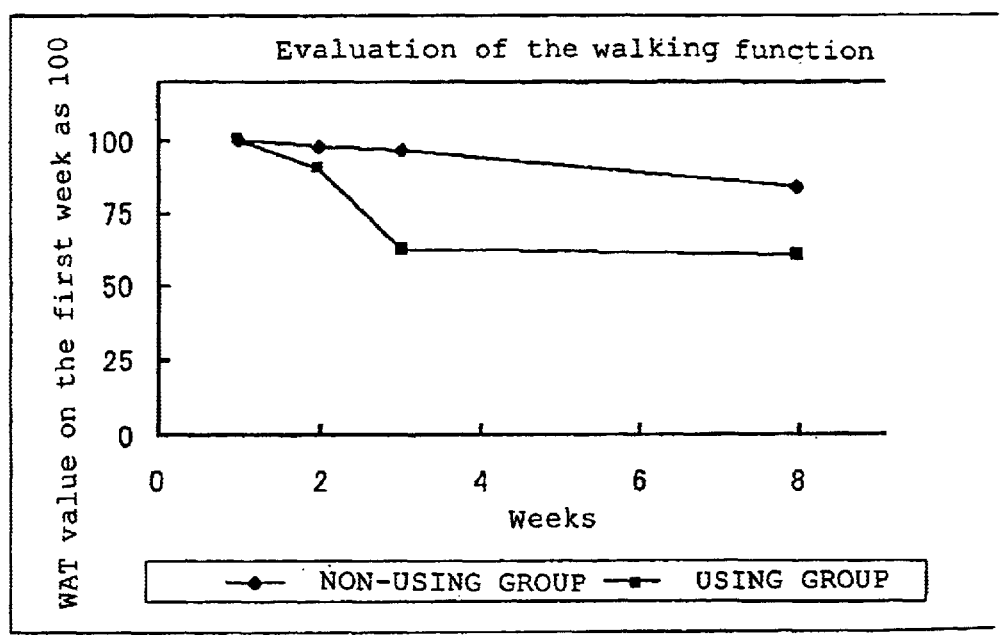
FIG. 5 is a drawing showing results of a walking function evaluation of the instrument for regenerating a living organism tissue or organ of the present invention.

As is apparent from FIG. 5, in the group of rats using the instrument for regenerating a tissue of the present invention, WTA value decreased rapidly toward the second or third weeks when taking the WTA value on the first week as 100. In contrast, in the group using no such instrument, almost no tendency of recovery was observed. That is, in the group using the instrument for regenerating a tissue, it was confirmed that the animal was rapidly able to walk on tiptoe on the foot on the side of the cut nerve, which indicates recovery of the nerve.

Figure 6:
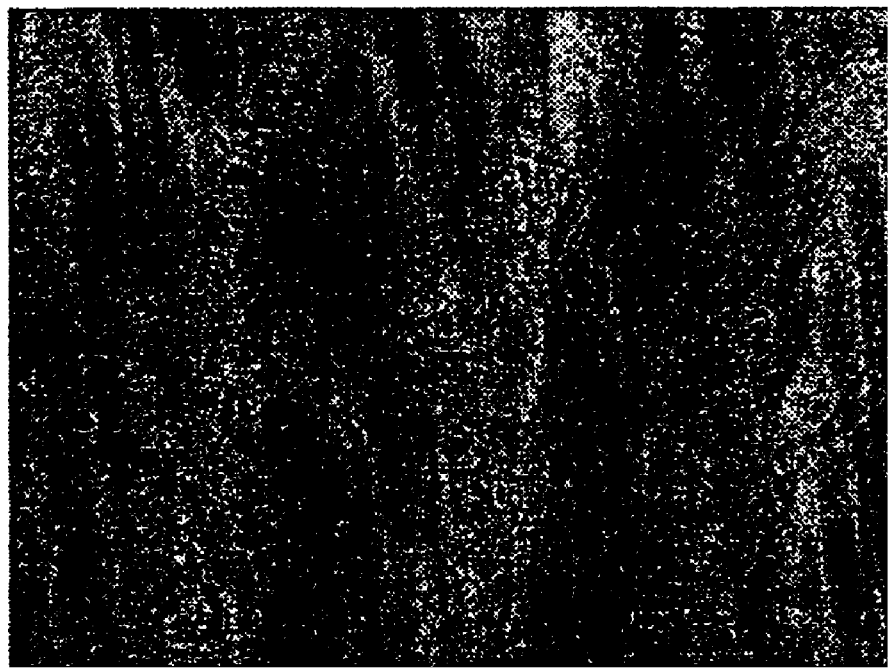
FIG. 6 is a photograph in lieu of a drawing, showing a stained figure of tissue at the twelfth week at the transplanted portion where the instrument for regenerating a living organism tissue or organ of the present invention is embedded.
Figure 7:
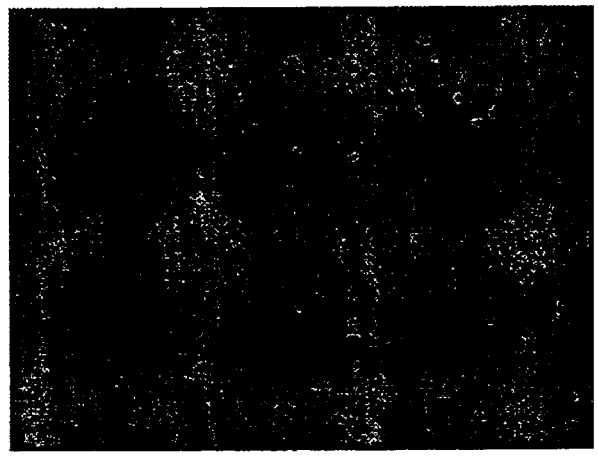
FIG. 7 is a photograph in lieu of a drawing, showing a stained figure at the twelfth week of an operated portion of a control instrument for regenerating a living organism tissue or organ of the present invention.

Then, nerve fiber regeneration was observed by cutting out the tissue at the site transplanted at the twelfth week from rats of the both groups and performing an immunological tissue staining. The results are shown in FIGS. 6 and 7. As is apparent from FIG. 6, in the group using the instrument for regenerating a tissue, the nerve regenerated in the form of fiber was stained and it was observed that the cut nerve was efficiently regenerated in the inside of the instrument for regenerating a tissue. In contrast, as is apparent from FIG. 7, in the group using no instrument for regenerating a tissue, it was observed that no regeneration of the fibrous nerve by invasion of a surrounding fibrous tissue occurred.

Figure 8:
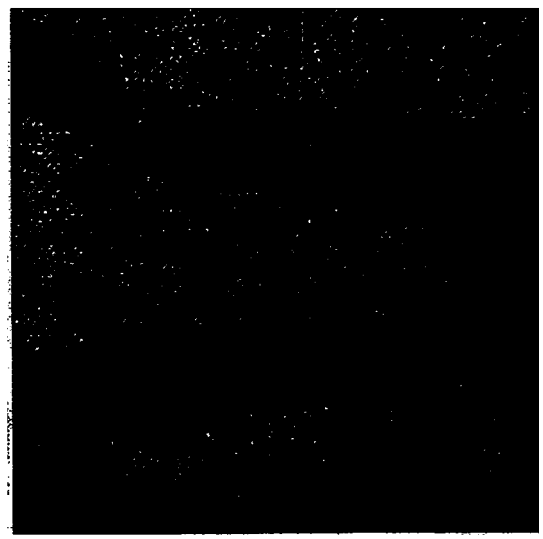
FIG. 8 is a photograph in lieu of a drawing, showing stained figures of a portion at the twelfth week where the instrument for regenerating a living organism tissue or organ of the present invention is embedded and substituted and of the peripheral side tissue subsequent to the substituted portion.

FIG. 8 is a diagram showing the results of staining the tissue on the peripheral side of the portion transplanted where the instrument for regenerating a tissue was embedded. In FIG. 8, the state of nerve fiber regeneration in the direction toward the peripheral side by use of the instrument for regenerating a tissue was observed in the portion on the right hand side of line A—A.

EXAMPLE 2

Tissue Regeneration Experiment on a Beagle

Using the regeneration instrument produced in Example 1, a tissue regeneration experiment on a beagle was conducted to confirm the regeneration of tissue under conditions close to that of humans. As for the tissue to be regenerated, a beagle peripheral nerve was selected.

The beagle fibular nerve was cut to make a 35 mm deficit portion. In this site the tubular collagen-made instrument for regenerating an organ mentioned above previously cut to 35 mm, i.e., the same length as the deficit portion length and subjected to 25-kGy $\gamma$-ray sterilization treatment was inserted and both ends thereof were sutured and fixed to the cut ends of the nerve with 8-0 polyamide based surgical suture at plural points.

Experimental Results

After the enthesis, an observation of nerve fiber regeneration was carried out by cutting out the tissue from the enthesis site at the time of the fifth week and performing an immunological tissue staining of protein gene product 9.5 (PGP 9.5).

An observation of nerve fiber regeneration was carried out by cutting out the nerve cut site from the beagle at the time of the fifth week after the experiment and performing an immunological tissue staining. The results obtained are shown in FIGS. 9, 10 and 11.

Figure 9:
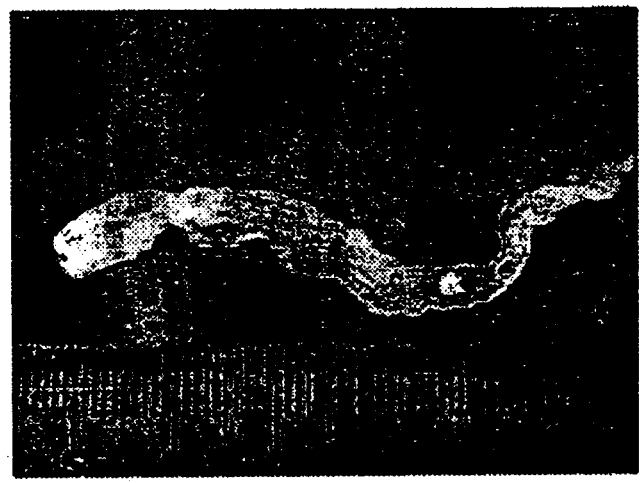
FIG. 9 is a photograph in lieu of a drawing, showing a portion of a nerve regenerated by the instrument for regenerating a living organism tissue or organ according to Example 2 of the present invention.

FIG. 9 is a view showing results of regeneration obtained by embedding the instrument for regenerating a tissue which is taken out on the fifth week. FIG. 10 is a photograph showing a stained cross section of a central portion of a peripheral nerve portion with the portion extending from the line A–A' towards the direction indicated by the arrow being a peripheral nerve tissue portion regenerated by the instrument for regenerating a tissue which was embedded thereon. FIG. 11 is a photograph showing a stained cross section of a peropheral portion of a peripheral nerve portion, with the portion extending from the line B–B' towards the direction indicated by the arrow being a peripheral nerve tissue portion regenerated by the instrument for regenerating a tissue which was embedded thereon.

Figure 10:
FIG. 10 is an enlarged photograph is lieu of a drawing, showing a cross section of a portion of a nerve regenerated by the instrument for regenerating a living organism tissue or organ according to Example 2 of the present invention.

As is apparent from FIG. 10, the nerve regenerated in the form of a fiber has been stained and it can be observed that the cut nerve was efficiently regenerated in the inside of the instrument for regenerating a tissue on the side extending from the line A–A' towards the direction indicated by the arrow.

Figure 11:
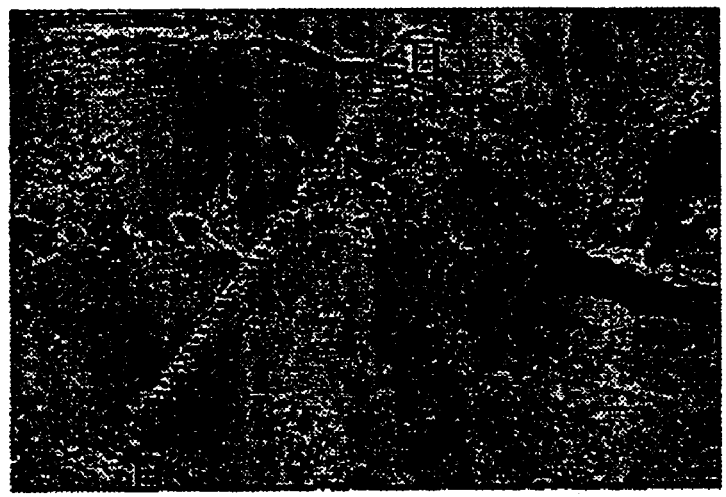
FIG. 11 is an enlarged photograph in lieu of a drawing, showing a cross section of a portion of a nerve regenerated by the instrument for regenerating a living organism tissue or organ of the present invention.

Further, FIG. 11 is a view showing the results obtained by staining the tissue on the peripheral end side of the connecting end part of the enthetic portion where the instrument for regenerating a tissue was embedded. In FIG. 11 the regenerated nerve tissue was also observed in the portion on the right hand side of the line B–B'. From this, the state of regeneration of the nerve tissue can be observed, in which the regenerated nerve tissue in the inside of the instrument for regenerating a tissue or organs is regenerated towards the peripheral side of the instrument for regenerating a tissue.

EFFECTS OF THE INVENTION

The instrument for regenerating a living tissue or organ of the present invention can regenerate and restore the target tissue or organ quickly and with certainty. In the case where the entire substance that constitutes the instrument for regeneration is constituted by collagen, it exerts excellent effects in that it exhibits good biocompatibility and after restoring the tissue, it is absorbed by the living organism leaving no residual foreign matter since it is made of a bioabsorbable material.

In the examples of the present invention, the instrument for regenerating a tissue of the invention is used for regenerating a peripheral nerve, but the instrument is also useful in the case where various tissues or organs such as a central nerve system, a ligament and a tendon are regenerated. By use of the instrument of the present invention, the structure of the fibrous material inside the instrument gives a footing of growth and directivity of growth to the cells being regenerated, thereby enabling the regeneration in a short period of time.

Therefore, the present invention exhibits excellent effects not only in regenerating nerve but also in regenerating other tissues or organs.

What is claimed is:

1. An instrument for regenerating a living organism tissue or organ, comprising a support (A) formed from a biodegradable material or a bioabsorbable material and, inside said support (A), a sponge-like fine matrix (B) formed from a biodegradable material or a bioabsorbable material and a linear channel (C) for guiding a living organism tissue or organ, wherein the living organism tissue or organ is a blood vessel, a trachea, an esophagus, an intestine, a tendon or ligament or a nerve of a human primate, a nonhuman primate or a rodent.

2. An instrument for regenerating a living organism tissue or organ according to claim 1, wherein the biodegradable material is decomposed by a decomposing enzyme in the living organism, an acid or an alkali, and is a protein, a polypeptide or a derivative thereof.

3. An instrument for regenerating a living organism tissue or organ according to claim 1, wherein each of the bioabsorbable materials is a porous substance which allows permeation of body fluid and is a protein, a polypeptide, or a derivative thereof, a polysaccharide or a derivative thereof, polylactic acid, polyglycolic acid, a copolymer of glycolic acid and lactic acid, a copolymer of lactic acid and $\epsilon$-aminocaproic acid or an aliphatic polyester.

4. An instrument for regenerating a living organism tissue or organ according to claim 1, wherein the support (A) formed from the biodegradable material or the bioabsorbable material is tubular.

5. An instrument for regenerating a living organism tissue or organ according to claim 1, wherein the support (A) formed from the biodegradable material or the bioabsorbable material is tubular and is constituted by a fibrous material.

6. An instrument for regenerating a living organism tissue or organ according to claim 5, wherein the fibrous material comprises short fibers, long fibers, filaments, a floc, a textile fabric, or a non-woven fabric.

7. An instrument for regenerating a living organism tissue or organ according to claim 1, wherein the sporous sponge matrix (B) is a collagen porous sponge matrix.

8. An instrument for regenerating a living organism tissue or organ according to claim 1, wherein the linear channel (C) for guiding the living organism tissue or organ comprises at least one fiber inserted into the inside of the support (A) in the longitudinal direction thereof.

9. An instrument for regenerating a living organism tissue or organ according to claim 1, wherein the linear channel (C) for guiding the living organism tissue or organ is at least one tubular structure and is formed in the inside of the support (A) in the longitudinal direction thereof.

10. An instrument for regenerating a living organism tissue or organ according to claim 1, wherein the linear channel (C) for guiding the living organism tissue or organ is embedded in the sponge-like fine matrix (B).

11. An instrument for regenerating a living organism tissue or organ according to claim 1, wherein the support (A) is a tubular structure comprising a bundle of collagen fibers, and the sponge-like fine matrix (B) is a collagen sponge layer provided in the inside of the tubular structure, and the linear channel (C) for guiding the living organism tissue or organ is a fiber or a tubular structure penetrating the collagen porous sponge matrix therethrough.

12. An instrument for regenerating a living organism tissue or organ according to claim 1, wherein the linear channel (C) for guiding a living organism tissue or organ is a channel for guiding regeneration of a peripheral or spinal nerve.

13. An instrument for regenerating a living organism tissue or organ, which comprises at least one linear structure (c) provided so as to penetrate a porous sponge matrix (b) therethrough in a longitudinal direction in the inside of a tubular structure (a), wherein tubular structure (a) is formed by a bundle of collagen fibers with a fiber diameter of about 5 to 1,000 $\mu$m, having an outer diameter of about 0.1 to 50 mm, and an inner diameter of about 0.05 to 40 mm, and porous sponge matrix (b) is a fine collagen sponge layer having a porosity of about 70 to 99.9% located inside the tubular structure.

14. An instrument for regenerating a living organism tissue or organ according to claim 13, wherein at least one linear structure (c) is formed from a collagen fiber having a fiber diameter of about 5 to 1,000 μm.

15. An instrument for regenerating a living organism tissue or organ according to claim 13, wherein the linear structure is provided with at least one tubular communicating passage having a pore diameter of about 5 to 1,000 μm.

16. An instrument for regenerating a living organism tissue or organ according to claim 14, wherein the linear structure is provided with at least one tubular communicating passage having a pore diameter of about 5 to 1,000 μm.

17. An instrument for regenerating a living organism tissue or organ according to claim 13, wherein the at least one linear structure (c) is a channel for guiding regeneration of a peripheral or spinal nerve.

* * * * *

UNITED STATES PATENT AND TRADEMARK OFFICE
CERTIFICATE OF CORRECTION

| | | |
|---|---|---|
| PATENT NO. | : 6,953,482 B2 | |
| APPLICATION NO. | : 10/132577 | |
| DATED | : October 11, 2005 | |
| INVENTOR(S) | : Nobutoshi Doi et al. | |

It is certified that error appears in the above-identified patent and that said Letters Patent is hereby corrected as shown below:

Column 11,
Line 64, "sponge-like fine" should be -- porous sponge --.

Column 12,
Line 31, "sporous" should be -- porous --.
Lines 46 and 50, "sponge-like fine" should be -- porous sponge --.

Signed and Sealed this

Twenty-seventh Day of June, 2006

JON W. DUDAS
*Director of the United States Patent and Trademark Office*